(12) United States Patent
Govari

(10) Patent No.: US 6,973,339 B2
(45) Date of Patent: Dec. 6, 2005

(54) LASSO FOR PULMONARY VEIN MAPPING AND ABLATION

(75) Inventor: Assaf Govari, Haifa (IL)

(73) Assignee: Biosense, Inc, New Brunswick, NJ (US)

( * ) Notice: Subject to any disclaimer, the term of this patent is extended or adjusted under 35 U.S.C. 154(b) by 146 days.

(21) Appl. No.: 10/629,661

(22) Filed: Jul. 29, 2003

(65) Prior Publication Data

US 2005/0033135 A1 Feb. 10, 2005

(51) Int. Cl.$^7$ .............. A61B 5/04; A61B 18/14
(52) U.S. Cl. .............. 600/374; 600/381; 128/899; 606/41
(58) Field of Search .............. 600/374, 381; 128/899; 606/41

(56) References Cited

U.S. PATENT DOCUMENTS

| | | |
|---|---|---|
| 4,649,924 A | 3/1987 | Taccardi |
| 4,940,064 A | 7/1990 | Desai |
| 5,239,999 A | 8/1993 | Imran |
| 5,297,549 A | 3/1994 | Beatty et al. |
| 5,311,866 A | 5/1994 | Kagan et al. |
| 5,385,146 A | 1/1995 | Goldreyer |
| 5,450,846 A | 9/1995 | Goldreyer |
| 5,487,391 A | 1/1996 | Panescu |
| 5,549,109 A | 8/1996 | Samson et al. |
| 5,582,609 A | 12/1996 | Swanson et al. |
| 5,662,108 A | 9/1997 | Budd et al. |
| 5,771,298 A | 6/1998 | Davis et al. |
| 5,807,395 A | 9/1998 | Mulier et al. |
| 5,848,972 A | 12/1998 | Triedman et al. |
| 5,916,213 A | 6/1999 | Haissaguerre et al. |
| 5,931,811 A | 8/1999 | Haissaguerre et al. |
| 5,931,835 A | 8/1999 | Mackey |
| 5,938,660 A | 8/1999 | Swartz et al. |
| 5,971,983 A | 10/1999 | Lesh |
| 6,012,457 A | 1/2000 | Lesh |
| 6,063,022 A | 5/2000 | Ben-Haim |
| 6,064,902 A | 5/2000 | Haissaguerre et al. |
| 6,068,629 A | 5/2000 | Haissaguerre et al. |
| 6,090,084 A | 7/2000 | Hassett et al. |
| 6,104,994 A | 8/2000 | Su et al. |
| 6,117,101 A | 9/2000 | Diederich et al. |
| 6,120,496 A | 9/2000 | Whayne et al. |
| 6,142,994 A | 11/2000 | Swanson et al. |
| 6,152,920 A | 11/2000 | Thompson et al. |

(Continued)

FOREIGN PATENT DOCUMENTS

EP 1 125 549 A2 8/2001

(Continued)

OTHER PUBLICATIONS

Partial European Search Report dated Dec. 6, 2004 for EP 04 25 4530.

(Continued)

*Primary Examiner*—Lee S. Cohen
(74) *Attorney, Agent, or Firm*—Louis J. Capezzuto

(57) ABSTRACT

A method is provided for electrical mapping of a pulmonary vein of a heart, including introducing into the heart a catheter having a curved section and a base section, the base section having a distal end attached to a proximal end of the curved section. At a location on the curved section, a first position signal is generated having fewer than six dimensions of position and orientation information. At a vicinity of the distal end of the base section, a second position signal is generated having six dimensions of position and orientation information. The method also includes measuring, at one or more locations on the curved section, an electrical property of the pulmonary vein.

46 Claims, 3 Drawing Sheets

U.S. PATENT DOCUMENTS

| | | |
|---|---|---|
| 6,164,283 A | 12/2000 | Lesh |
| 6,190,382 B1 | 2/2001 | Ormsby et al. |
| 6,217,528 B1 | 4/2001 | Koblish et al. |
| 6,227,371 B1 | 5/2001 | Song |
| 6,235,025 B1 | 5/2001 | Swartz et al. |
| 6,245,064 B1 | 6/2001 | Lesh et al. |
| 6,251,109 B1 | 6/2001 | Hassett et al. |
| 6,264,654 B1 | 7/2001 | Swartz et al. |
| 6,267,760 B1 | 7/2001 | Swanson |
| 6,272,371 B1 | 8/2001 | Shlomo |
| 6,290,699 B1 | 9/2001 | Hall et al. |
| 6,308,093 B1 | 10/2001 | Armoundas et al. |
| 6,332,880 B1 | 12/2001 | Yang et al. |
| 6,332,881 B1 | 12/2001 | Carner et al. |
| 6,400,981 B1 * | 6/2002 | Govari ................. 600/509 |
| 2002/0065455 A1 | 5/2002 | Ben-Haim et al. |
| 2002/0165448 A1 * | 11/2002 | Ben-Haim et al. .......... 600/424 |
| 2003/0018251 A1 * | 1/2003 | Solomon ................ 600/427 |
| 2003/0114846 A1 * | 6/2003 | Fuimaono et al. ............ 606/41 |
| 2004/0015164 A1 * | 1/2004 | Fuimaono et al. ............ 606/45 |
| 2004/0039293 A1 * | 2/2004 | Porath et al. ............... 600/509 |
| 2004/0193239 A1 * | 9/2004 | Falwell et al. .............. 607/122 |

FOREIGN PATENT DOCUMENTS

| | | |
|---|---|---|
| WO | WO 96/05768 A1 | 2/1996 |
| WO | WO 02/082375 A2 | 10/2002 |

OTHER PUBLICATIONS

US 6,348,062, 02/2002, Hopkins et al. (withdrawn)

* cited by examiner

LASSO FOR PULMONARY VEIN MAPPING AND ABLATION

FIELD OF THE INVENTION

The present invention relates generally to intrabody mapping systems, and specifically to methods and devices for electrophysiological mapping of intracardiac sites to facilitate therapeutic procedures.

BACKGROUND OF THE INVENTION

Cardiac arrhythmia, such as atrial fibrillation, occurs when regions of cardiac tissue abnormally conduct electric signals to adjacent tissue, thereby disrupting the normal cardiac cycle and causing asynchronous rhythm. The primary sources of undesired signals are located in the tissue region along the pulmonary veins of the left atrium and in the superior pulmonary veins. After unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

A number of approaches have been described for acquiring cardiac electrical data using single- and multi-electrode catheters. U.S. Pat. No. 5,487,391 to Panescu, U.S. Pat. No. 5,848,972 to Triedman et al., U.S. Pat. No. 4,649,924 to Taccardi, U.S. Pat. No. 5,311,866 to Kagan et al., U.S. Pat. No. 5,297,549 to Beatty et al., U.S. Pat. Nos. 5,385,146 and 5,450,846 to Goldreyer, U.S. Pat. No. 5,549,109 to Samson et al., U.S. Pat. No. 5,711,298 to Littmann et al., and U.S. Pat. No. 5,662,108 to Budd et al., all of which are incorporated herein by reference, are typical examples of methods proposed for mapping electrical characteristics of the heart utilizing catheter-mounted electrodes.

U.S. Pat. No. 5,807,395 Mulier et al. and U.S. Pat. No. 6,190,382 to Ormsby et al., which are incorporated herein by reference, describe systems for ablating body tissue using radio frequency. U.S. Pat. Nos. 6,090,084 and 6,251,109 to Hassett et al., U.S. Pat. No. 6,117,101 to Diederich et al., U.S. Pat. No. 5,938,660 to Swartz et al., U.S. Pat. Nos. 6,245,064 and 6,024,740 to Lesh et al., U.S. Pat. Nos. 5,971,983, 6,012,457 and 6,164,283 to Lesh, U.S. Pat. No. 6,004,269 to Crowley et al., and U.S. Pat. No. 6,064,902 to Haissaguerre et al., all of which are incorporated herein by reference, describe apparatus for tissue ablation to treat atrial arrhythmia, primarily tissue located within the pulmonary veins or on the ostia of the pulmonary veins. U.S. Pat. Nos. 5,582,609 and 6,142,994 to Swanson et al., U.S. Pat. No. 6,152,920 to Thompson et al., U.S. Pat. No. 6,120,496 to Whayne et al., and U.S. Pat. No. 6,267,760 to Swanson, all of which are incorporated herein by reference, describe techniques for positioning therapeutic elements within the body, and ablating and forming incisions in soft tissue.

U.S. Pat. No. 6,104,944 to Martinelli, which is incorporated herein by reference, describes a method for navigating a catheter that includes locatable electrode elements distributed along the catheter. The locatable electrode elements include at least two navigated electrode elements and one or more virtually navigable electrode elements located relative to the navigated electrode elements. Location data are provided for the navigated electrode elements, and location data for the virtually navigable electrode elements are determined as a function of the location data for the navigated electrode elements.

Pre-shaped catheters have been developed to assist with positioning within the body. These catheters may be shaped to specifically access a particular site within the heart. For U.S. Pat. Nos. 5,779,669 and 5,931,811 to Haissaguerre et al., which are incorporated herein by reference, describe a steerable catheter, particularly for use in the heart, which comprises a pre-shaped loop with a flexible middle section that bends in response to forces applied by a steering device. The steerable catheter is advanced into the patient until a complexly curved section of the catheter is seated relative to an anatomical feature within the patient. The complexly curved section generally corresponds in shape to the anatomical feature against which the catheter is to be seated. Once seated, a pulling force is applied to a wire to cause a flexible intermediate section of the catheter to flex and thereby entrain a distal end of the catheter into contact with a desired site within the patient. Embodiments of this catheter contain electrodes and temperature sensors, such that the catheter can be used for recording, mapping, stimulation or ablation. Based on the apparatus described in the '669 and '811 patents, Biosense Webster developed the LASSO Circular Mapping Catheter, a catheter capable of circumferentially mapping pulmonary veins.

U.S. Pat. No. 6,063,022 to Ben-Haim, which is assigned to the assignee of the present patent application and is incorporated herein by reference, describes an invasive probe including two position sensors in a fixed, known relation to the distal end of the probe. The position sensors generate signals responsive to their respective position coordinates and at least one contact sensor along a radial surface of the probe for generating a signal representing its contact with body tissue to be ablated by electrodes on the probe.

U.S. Pat. No. 6,272,371 to Ben-Haim, which is assigned to the assignee of the present patent application and is incorporated herein by reference, describes an invasive probe including a flexible portion that assumes a predetermined curve form when a force is applied thereto. Two position sensors, fixed to the distal portion of the probe in known positions, are used to determine position and orientation coordinates of at least one of the sensors, and to determine the locations of a plurality of points along the length of the distal portion of the probe.

PCT Patent Publication WO 96/05768 and corresponding U.S. Patent Application Publication 2002/0065455 to Ben-Haim et al., which are assigned to the assignee of the present patent application and which are incorporated herein by reference, describe a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six position and orientation dimensions, so that the position and orientation of the catheter are known without the need for imaging the catheter.

The following patents, which are incorporated herein by reference, may be of interest:

U.S. Pat. No. 6,348,062, entitled, "Vascular device having one or more articulation regions and methods of use"

U.S. Pat. No. 6,332,880, entitled, "Loop structures for supporting multiple electrode elements"

U.S. Pat. No. 6,332,881, entitled, "Surgical ablation tool"

U.S. Pat. No. 6,308,093, entitled, "Method and apparatus for guiding ablative therapy of abnormal biological electrical excitation"

U.S. Pat. No. 6,290,699, entitled, "Ablation tool for forming lesions in body tissue"

U.S. Pat. No. 6,264,654, entitled, "Ablation catheter"

U.S. Pat. No. 6,235,025, entitled, "Process and device for the treatment of atrial arrhythmia"

U.S. Pat. No. 6,217,528, entitled, "Loop structure having improved tissue contact capability"

U.S. Pat. No. 6,068,629, entitled, "System and methods for tissue mapping and ablation"

U.S. Pat. No. 5,931,835, entitled, "Radio frequency energy delivery system for multipolar electrode catheters"

U.S. Pat. No. 5,916,213, entitled, "Systems and methods for tissue mapping and ablation"

U.S. Pat. No. 5,239,999, entitled, "Helical endocardial catheter probe"

U.S. Pat. No. 4,940,064, entitled, "Catheter for mapping and ablation and method therefore"

SUMMARY OF THE INVENTION

It is an object of some aspects of the present invention to provide apparatus and methods to increase the accuracy with which electrophysiological properties of the heart are mapped.

It is also an object of some aspects of the present invention to provide apparatus and methods for positioning operative elements, such as ablation electrodes, within a pulmonary vein (PV).

It is a further object of some aspects of the present invention to provide improved apparatus and methods for real-time, accurate, simultaneous determination of the location of a plurality of electrophysiological sensing elements mounted on an intracardiac catheter.

It is yet a further object of some aspects of the present invention to provide apparatus and methods for reducing the time required for mapping electrophysiological properties of the heart.

It is still a further object of some aspects of the present invention to provide apparatus and methods for intracardiac mapping which can readily be integrated into existing mapping support systems and methods, in order to increase the accuracy of these systems and methods.

In preferred embodiments of the present invention, apparatus for circumferentially mapping a pulmonary vein (PV) comprises a catheter that includes a curved section of a known fixed length, preferably shaped to generally conform to the shape of the interior surface of the PV. The curved section comprises one or more sensing electrodes, and its proximal end is joined at a fixed or generally known angle to a base section of the catheter, or at an angle whose range is limited. Preferably, at least one single-coil five-dimensional position sensors is fixed to the curved section of the catheter. Most preferably, two single-coil five-dimensional position sensors are fixed to the curved section, one at the distal end and one approximately at the center of the curve. A multi-coil six-dimensional position sensor is preferably fixed to the distal end of the base section, proximate to the joint with the curved section. The catheter is inserted into the heart, and the curved section is positioned in essentially continuous contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV.

Advantageously, the single-coil position sensors, which are generally substantially smaller than the multi-coil position sensor, are fixed to the curved section, which preferably is relatively small in order to be readily placed in the PV. The larger multi-coil position sensor is fixed to the base section, which can be relatively large because it remains within the atrium. Six-dimensional information from the multi-coil position sensor, combined with the generally known angle of the joint and predetermined flexing behavior of the curved section, compensates for the more limited information from the single-coil position sensors. The resulting accurate position information for the sensing electrodes enables high-resolution electrophysiological mapping of the PV and accurate location of regions of abnormal electrical behavior.

In some preferred embodiments of the present invention, upon completion of electrophysiological mapping, the mapping catheter is removed from the heart. Responsive to the measured PV potentials, target tissue is selected for ablation in order to treat the arrhythmia. The target tissue is ablated using methods and apparatus known in the art, such as those described in the references cited hereinabove. Optionally, the mapping catheter is reinserted into the PV after the completion of ablation, in order to confirm that the ablation has terminated signals causing arrhythmia, such as by achieving bi-directional block.

Alternatively, in some preferred embodiments of the present invention, the sensing electrodes on the mapping catheter are adapted to additionally perform ablation of selected sites, or the mapping catheter further comprises ablation elements, thereby eliminating the need for separate ablation apparatus. Preferably, the termination of the abnormal electrical activity is confirmed using the sensing electrodes prior to removal of the mapping catheter.

There is therefore provided, in accordance with an embodiment of the present invention, apparatus for electrical mapping of a pulmonary vein of a heart, including a catheter, which includes:

a curved section including a single-coil position sensor, and one or more electrodes, adapted to measure an electrical property of the pulmonary vein; and a base section having a distal end attached to a proximal end of the curved section, the base section including a multi-coil position sensor within 3 mm of the distal end thereof.

The multi-coil position sensor is typically positioned within 1 mm of the distal end of the base section.

For some applications, the curved section includes a material that is flexible, and maintains a substantially fixed length of the curved section. In an embodiment, the curved section has an elasticity that is generally constant over at least a quarter of the curved section.

In an embodiment, the multi-coil position sensor includes exactly two coils. Alternatively, the multi-coil position sensor includes exactly three coils.

For some applications, the catheter includes one or more ablation elements. Alternatively or additionally, at least one of the electrodes is adapted to perform ablation.

In an embodiment, the single-coil position sensor is positioned in a vicinity of a distal end of the curved section. Alternatively or additionally, the curved section includes a center single-coil position sensor in a vicinity of a center thereof.

The curved section is typically shaped to generally conform to a shape of an interior surface of the pulmonary vein.

For some applications, the apparatus includes a processor, adapted to calculate respective six-dimensional position and orientation coordinates of the one or more electrodes, responsive to respective position signals generated by the single-coil and multi-coil position sensors. Alternatively or additionally, the apparatus includes a processor, adapted to generate an electrophysiological map of the pulmonary vein responsive to respective position signals generated by the single-coil and multi-coil position sensors, and responsive to the electrical property.

In an embodiment, the multi-coil position sensor includes two or more non-concentric coils. In this case, the two or more non-concentric coils are typically arranged so as to be mutually orthogonal.

There is further provided, in accordance with an embodiment of the present invention, apparatus for electrical mapping of a pulmonary vein of a heart, including a catheter, which includes:

a curved section including a first position sensor, capable of generating fewer than six dimensions of position and orientation information, and one or more electrodes, adapted to measure an electrical property of the pulmonary vein; and a base section having a distal end attached to a proximal end of the curved section, the base section including, within 3 mm of the distal end thereof, a second position sensor, capable of generating six dimensions of position and orientation information.

In an embodiment, the first position sensor is capable of generating exactly five dimensions of position and orientation information.

There is yet further provided, in accordance with an embodiment of the present invention, apparatus for electrical mapping of a pulmonary vein of a heart, including a catheter, which includes:

a curved section including a first position sensor in a vicinity of the distal end, capable of generating fewer than six dimensions of position and orientation information, and one or more electrodes, adapted to measure an electrical property of the pulmonary vein;

a base section having a distal end attached to a proximal end of the curved section, the base section including, within 3 mm of the distal end thereof, a second position sensor, capable of generating six dimensions of position and orientation information; and a processor, adapted to generate an electrophysiological map of the pulmonary vein responsive to respective position signals generated by the first and second position sensors, and responsive to the electrical property.

In an embodiment, the processor is adapted to calculate respective six-dimensional position and orientation coordinates of the one or more electrodes, responsive to the respective position signals.

There is still further provided, in accordance with an embodiment of the present invention, apparatus for electrical mapping of a chamber of a body of a subject, including a catheter, which includes:

a curved section including a first position sensor, capable of generating fewer than six dimensions of position and orientation information, and one or more electrodes, adapted to measure an electrical property of the chamber; and a base section having a distal end attached to a proximal end of the curved section, the base section including, within 3 mm of the distal end thereof, a second position sensor, capable of generating six dimensions of position and orientation information.

There is also provided, in accordance with an embodiment of the present invention, a method for electrical mapping of a pulmonary vein of a heart, including:

introducing into the heart a catheter having a curved section and a base section, the base section having a distal end attached to a proximal end of the curved section;

generating, at a location on the curved section, a first position signal having fewer than six dimensions of position and orientation information, and, at a vicinity of the distal end of the base section, a second position signal having six dimensions of position and orientation information; and measuring, at one or more locations on the curved section, an electrical property of the pulmonary vein.

Typically, the method includes generating an electrophysiological map of the pulmonary vein responsive to the first position signal, the second position signal, and the electrical property. Alternatively or additionally, ablating the tissue includes determining a location of an electrical abnormality in the tissue responsive to the first position signal, the second position signal, and the electrical property, and ablating the tissue substantially at the location.

In an embodiment, introducing the catheter into the heart includes positioning the curved section within the pulmonary vein. In this case, positioning the curved section within the pulmonary vein typically includes positioning the base section within a left atrium of the heart. Additionally, positioning the curved section within the pulmonary vein typically includes generally maintaining a point of attachment of the curved and base sections in a vicinity of an ostium of the pulmonary vein while mapping the pulmonary vein.

There is still further provided, in accordance with an embodiment of the present invention, a method for electrical mapping of a chamber of a body of a subject, including:

introducing into the chamber a catheter having a curved section and a base section, the base section having a distal end attached to a proximal end of the curved section;

generating, at a location on the curved section, a first position signal having fewer than six dimensions of position and orientation information, and, at a vicinity of the distal end of the base section, a second position signal having six dimensions of position and orientation information; and measuring, at one or more locations on the curved section, an electrical property of the chamber.

The present invention will be more fully understood from the following detailed description of the preferred embodiments thereof, taken together with the drawing, in which:

DETAILED DESCRIPTION OF PREFERRED EMBODIMENTS

Figure 1:
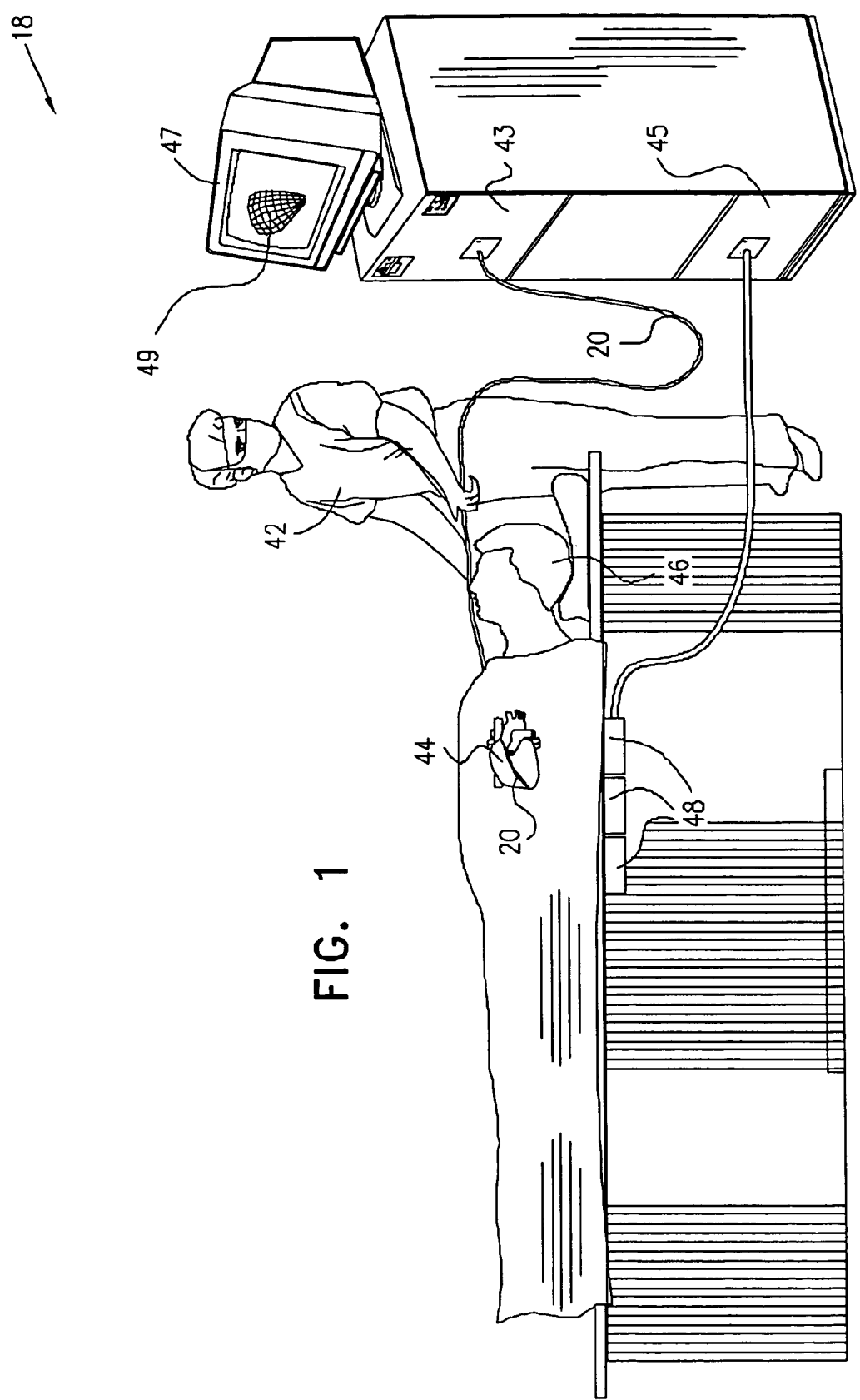
FIG. 1 is a schematic, pictorial illustration of a mapping system, for mapping of electrical activity in a pulmonary vein, in accordance with a preferred embodiment of the present invention.

FIG. 1 is a schematic, pictorial illustration of a mapping system 18, for mapping of electrical activity in a pulmonary vein of a heart 44 of a subject 46, in accordance with a preferred embodiment of the present invention. System 18 comprises a catheter 20, which is inserted by a user 42 through a vein or artery of the subject into a pulmonary vein of the heart. Preferably, system 18 further comprises a console 43.

Figure 2:
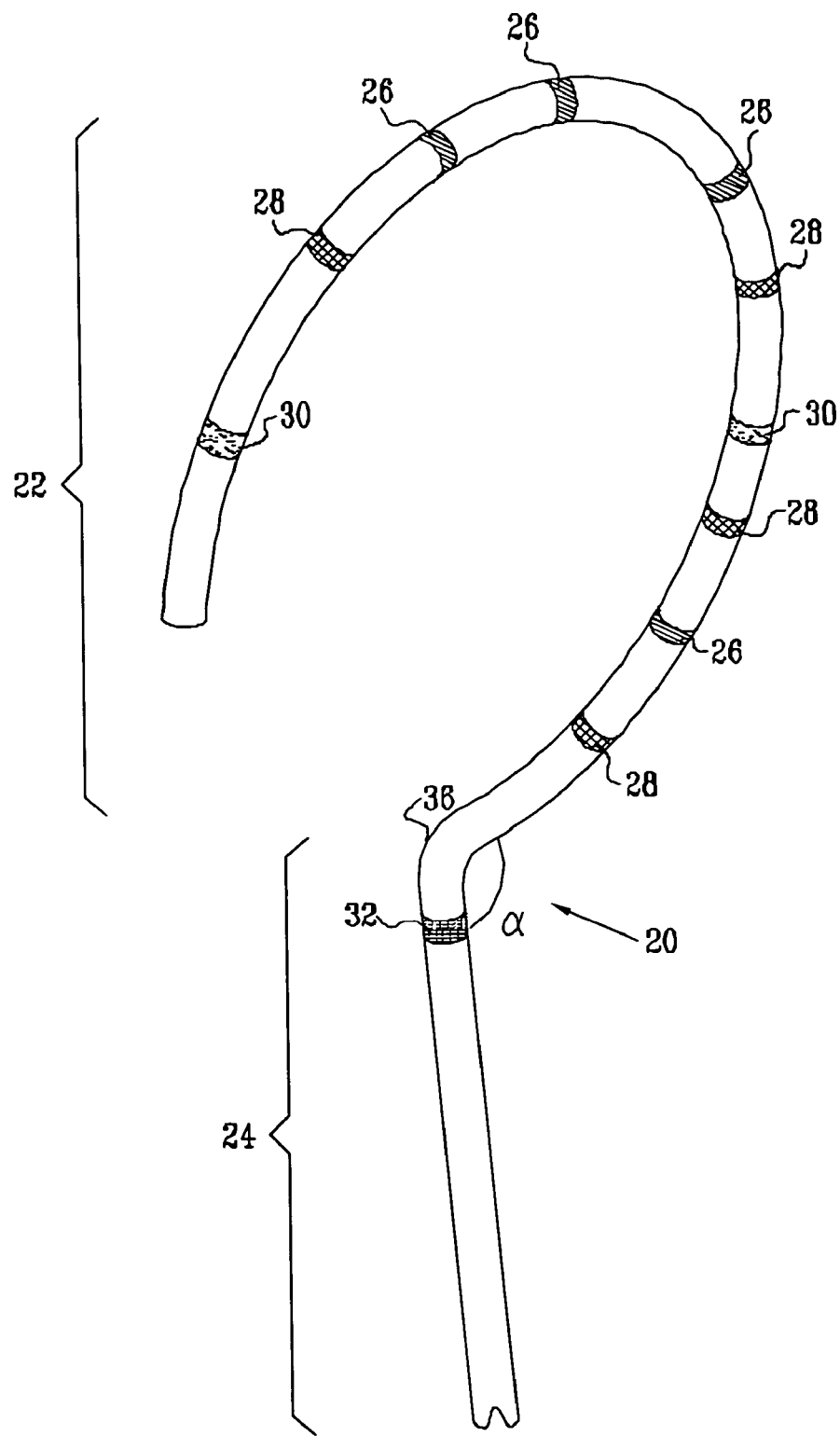
FIG. 2 is a simplified pictorial representation of a cardiac diagnostic and therapeutic system, in accordance with a preferred embodiment of the present invention.

FIG. 2 is a schematic, pictorial illustration showing a distal portion of catheter 20, for facilitating accurate electrophysiological mapping of a pulmonary vein (PV) in order to enable therapeutic ablation. Catheter 20 comprises a curved section 22 joined at a generally known or range-restricted angle alpha to a base section 24, at a joint 36. Joint 36 may define the point where two initially-separate members (sections 22 and 24) are joined, or, alternatively, the joint may define the point on catheter 20 where a single member is bent, so as to form base section 24 and curved section 22. Curved section 22 is of a known fixed length, and comprises material that preferably is twistable but not stretchable when subjected to typical forces. Preferably, curved section 22 is sufficiently resilient so as to assume a predetermined, curved form, when no force is applied thereto, and to be deflected from the predetermined curved form when a force is applied thereto. Preferably, curved section 22 has an elasticity that is generally constant over at least a portion of its length, for example, because of internal reinforcement of the curved section with a resilient longitudinal member, as is known in the art. One or more sensing electrodes 26, adapted for sensing electrical characteristics of PV tissue, are fixed to curved section 22.

Preferably, at least one single-coil position sensor 30 is fixed to curved section 22. Most preferably, a first single-coil position sensor 30 is fixed to the distal end of curved section 22 (distal with respect to base section 24), and a second single-coil position sensor 30 is fixed to the approximate center of curved section 22. Optionally, one or more additional single-coil position sensors 30 are fixed to curved section 22. Additionally, a multi-coil position sensor 32 is preferably fixed near the distal end of base section 24, in the vicinity of joint 36. Multi-coil position sensor 32 is preferably able to generate six position and orientation dimensions, using techniques described in the above-cited PCT Patent Publication to Ben-Haim et al., or other techniques known in the art. Multi-coil position sensor 32 preferably comprises two or three coils, which are generally sufficient for generating six dimensions of position information. Single-coil position sensor 30 is preferably able to generate five position and orientation dimensions. A preferred electromagnetic mapping sensor is manufactured by Biosense Webster (Israel) Ltd., (Tirat Hacarmel, Israel) and marketed under the trade designation NOGA™. Alternatively, single-coil and multi-coil positions sensors 30 and 32 comprise field sensors other than coils, such as Hall effect devices or other antennae, in which case position sensors 30 are preferably smaller than position sensor 32.

Position sensors 30 and 32 are fixed to catheter 20 by any suitable method, for example, using polyurethane glue or the like. The position sensors are electrically connected to an electromagnetic sensor cable (not shown), which extends through the catheter body and into a control handle of the catheter. The electromagnetic sensor cable preferably comprises multiple wires encased within a plastic covered sheath. Within the catheter body, the sensor cable may be enclosed within a protective sheath along with lead wires of sensing electrodes 26, if desired. Preferably, in the control handle, the wires of the sensor cable are connected to a circuit board (not shown), which amplifies the signals received from the position sensors and transmits them to a computer housed in console 43 (FIG. 1), in a form understandable to the computer. Alternatively, amplifying circuitry is included at the distal end of catheter 20, so as to reduce the effect of noise.

Reference is again made to FIG. 1. In a preferred embodiment of the present invention, to use position sensors 30 and 32, the subject is placed in a magnetic field generated, for example, by situating under the subject a pad containing field generator coils 48 for generating a magnetic field. A reference electromagnetic sensor (not shown) is preferably fixed relative to the subject, e.g., taped to the subject's back, and catheter 20 containing the position sensors is advanced into the subject's heart and into one of the pulmonary veins. The coils in the position sensors generate weak electrical signals indicative of their position in the magnetic field. Signals generated by both the fixed reference sensor and position sensors in the heart are amplified and transmitted to console 43, which analyzes the signals so as to facilitate the determination and visual display of the precise location of position sensors 30 and 32 relative to the reference sensor.

Each of position sensors 30 preferably comprises one coil, and position sensor 32 preferably comprises three non-concentric, typically mutually-orthogonal coils, such as those described in the above-cited PCT Patent Publication WO 96/05768. The coils sense magnetic fields generated by field generator coils 48, which are driven by driver circuits 45 (FIG. 1). Alternatively, the sensors may generate fields, which are detected by coils 48. System 18 thus achieves continuous generation of five dimensions of position and orientation information with respect to each of position sensors 30, and six dimensions with respect to position sensor 32.

As noted above, catheter 20 is coupled to console 43, which enables the user to observe and regulate the functions of the catheter. Console 34 includes a processor, preferably a computer with appropriate signal processing circuits. The processor is coupled to drive a monitor 47. The signal processing circuits typically receive, amplify, filter and digitize signals from catheter 20, including signals generated by position sensors 30 and 32 and sensing electrodes 26. The digitized signals are received and used by the console to compute the position and orientation of the catheter and to analyze the electrical signals from the electrodes. The information derived from this analysis is used to generate an electrophysiological map 49 of a pulmonary vein (PV) of the subject, typically in order to facilitate therapeutic ablation.

Typically, system 18 includes other elements, which are not shown in the figures for the sake of simplicity. For example, system 18 may include an ECG monitor, coupled to receive signals from one or more body surface electrodes, so as to provide an ECG synchronization signal to console 43. As mentioned above, the system typically also includes a reference position sensor, either on an externally-applied reference patch attached to the exterior of the subject's body, or on an internally-placed catheter, which is inserted into heart 44 and maintained in a fixed position relative to the heart. By comparing the position of catheter 20 to that of the reference catheter, the coordinates of catheter 20 are accurately determined relative to the heart, irrespective of heart motion. Alternatively, any other suitable method may be used to compensate for heart motion.

Figure 3:
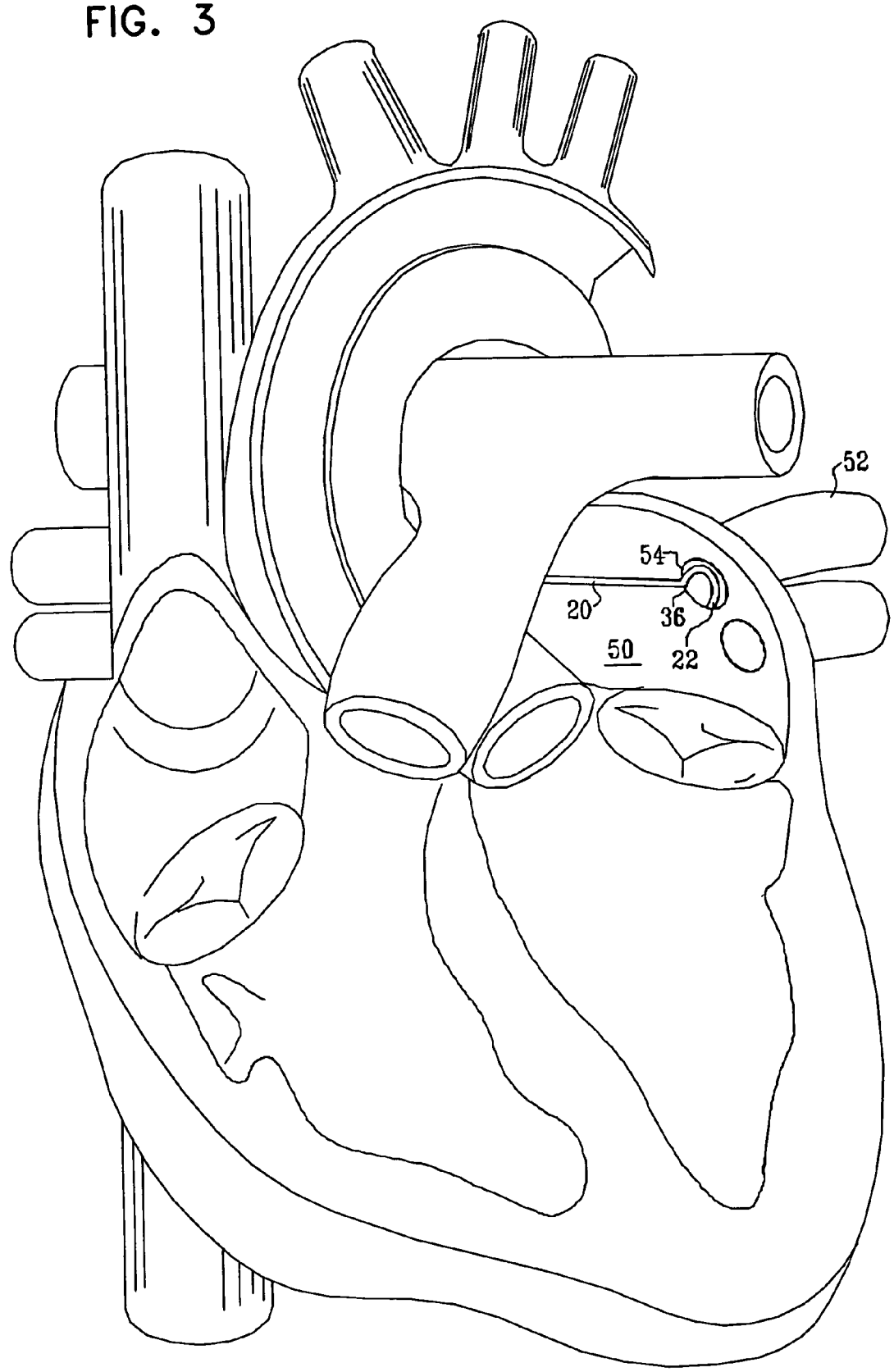
FIG. 3 is a schematic, sectional illustration of a portion of a left atrium of the heart, showing the distal portion of the catheter of FIG. 2 partially inserted into a pulmonary vein, in accordance with a preferred embodiment of the present invention.

FIG. 3 is a schematic, sectional illustration of a portion of a left atrium 50 of heart 44, showing the distal portion of catheter 20 partially inserted into a pulmonary vein 52, in accordance with a preferred embodiment of the present invention. During a procedure, catheter 20 is advanced into left atrium 50, and joint 36 is placed at or near an ostium 52 of PV 52 so that curved section 22 is within the PV and in substantially continuous contact with the tissue of the wall of the PV. The computer housed in console 43 determines the five-dimensional dispositions of single-coil position sensors 30, and the six-dimensional disposition of multi-coil position sensor 32. Using these determined positions, the generally known measurement of angle alpha, the length of curved section 22, and the generally known flexing behavior of curved section 22, control unit 40 preferably calculates the six-dimensional position and angle coordinates of sensing electrodes 26. Alternatively, other calculation techniques, as will be evident to one skilled in the art having read this application, are used.

Typically, the positions of sensing electrodes 26 and the electrical data measured by sensing electrodes 26 are used in combination to determine the location of electrical abnormalities in PV tissue, and to select target tissue to which ablation can be usefully and accurately applied in order to create non-conducting lesions so as to interrupt the inappropriate conduction pathways, and/or to terminate the electrical abnormalities. In a preferred embodiment of the present invention, catheter 20 is removed upon the completion of electrophysiological mapping, and the target tissue is ablated using methods and apparatus known in the art, such as those described in one or more of the references cited hereinabove. Alternatively, a catheter similar to catheter 20, but comprising ablation elements instead of sensing electrodes, is used to perform this ablation. Optionally, catheter 20 is reinserted into the PV after the completion of ablation, in order to confirm that the ablation has blocked or terminated the signals causing arrhythmia.

Alternatively or additionally, sensing electrodes 26 are adapted to additionally perform ablation, or catheter 20 further comprises ablation elements 28 fixed thereto, thereby generally eliminating the need for insertion of dedicated ablation apparatus. Ablation elements 28 are preferably electrodes that perform ablation using radiofrequency energy. Alternatively, ablation elements 28 perform ablation by applying other local treatments, such as by applying ultrasound or laser energy, or by applying a cryogenic treatment. Preferably, each element adapted to perform ablation (whether a sensing electrode 26 or an ablation element 28) has an associated temperature sensor incorporated therein or separate therefrom, for sensing temperature at the surface where ablation is being performed. Control unit 40 preferably uses the sensed temperatures to regulate the supplied energy, and thereby generally maintain the ablation temperature at a desired level. Preferably, the blocking or termination of the abnormal electrical activity is confirmed using sensing electrodes 26 prior to removal of catheter 20.

In a preferred embodiment, ablation elements 28 and sensing electrodes 26 are preferably attached to catheter 20 and operative, mutatis mutandis, in accordance with one of the arrangements described in European Patent Application EP 1 125 549 and corresponding U.S. patent application Ser. No. 09/506,766 to Ben-Haim et al., which are assigned to the assignee of the present application and which are incorporated herein by reference. Alternatively or additionally, the electrodes may comprise ring electrodes, or substantially any other suitable type of surface electrodes, as are known in the art.

In a preferred embodiment of the present invention, apparatus for accurately mapping electrophysiological characteristics of the heart comprises a Biosense Webster LASSO Circular Mapping Catheter. Typically, in this embodiment, 10–12 sensing electrodes are located on the curved and flexible distal section of the catheter, one single-coil five-dimensional location sensor is located on the distal end of the distal section, and one single-coil five-dimensional location sensor is located at the proximal end or near the center of the distal section. The three-coil six-dimensional location sensor is placed on the base section proximate to the point of connection with the complexly curved proximal section.

Advantageously, position sensors 30, which are generally substantially smaller than position sensor 32, are fixed to curved section 22, which preferably is relatively small in order to be readily placed in the PV. Larger position sensor 32 is fixed to base section 24, which can be relatively large because it remains within the atrium. Six-dimensional information from position sensor 32, combined with the generally known angle of joint 36 and predetermined flexing behavior of curved section 22, compensates for the more limited information from position sensors 30. The resulting accurate position information for sensing electrodes 26 enables high-resolution electrophysiological mapping of the PV and accurate location of regions of abnormal electrical behavior.

It is to be understood that whereas preferred embodiments of the present invention are generally described hereinabove with respect to accurately mapping the electrical characteristics of pulmonary veins, the scope of the present invention includes applying analogous techniques to other areas of the body wherein accurate mapping of particular characteristics can be useful in enabling therapeutic techniques.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. Apparatus for electrical mapping of a pulmonary vein of a heart, comprising:
   (a) a catheter, which comprises:
      (i) a curved section comprising a single-coil position sensor for generating five position and orientation dimensions, and one or more electrodes, adapted to measure an electrical property of the pulmonary vein; and
      (ii) a base section having a distal end attached to a proximal end of the curved section, the base section comprising a multi-coil position sensor within 3 mm of the distal end thereof for generating six position and orientation dimensions; and (b) a computer for determining five-dimensional dispositions of the single-coil position sensor and six-dimensional dispositions of the multi-coil position sensor and combining the electrical property of the pulmonary vein for determining electrical abnormalities in the pulmonary vein for selecting target tissue to ablate in the pulmonary vein.

2. The apparatus according to claim 1, wherein the multi-coil position sensor is positioned within 1 mm of the distal end of the base section.

3. The apparatus according to claim 1, wherein the curved section comprises a material that is flexible, and maintains a substantially fixed length of the curved section.

4. The apparatus according to claim 1, wherein the curved section has an elasticity that is generally constant over at least a quarter of the curved section.

5. The apparatus according to claim 1, wherein the multi-coil position sensor comprises exactly two coils.

6. The apparatus according to claim 1, wherein the multi-coil position sensor comprises exactly three coils.

7. The apparatus according to claim 1, wherein the catheter comprises one or more ablation elements.

8. The apparatus according to claim 1, wherein at least one of the electrodes is adapted to perform ablation.

9. The apparatus according to claim 1, wherein the single-coil position sensor is positioned in a vicinity of a distal end of the curved section.

10. The apparatus according to claim 1, wherein the curved section comprises a center single-coil position sensor in a vicinity of a center thereof.

11. The apparatus according to claim 1, wherein the curved section is shaped to generally conform to a shape of an interior surface of the pulmonary vein.

12. The apparatus according to claim 1, wherein the computer generates an electrophysiological map of the pulmonary vein responsive to respective position signals generated by the single-coil and multi-coil position sensors, and responsive to the electrical property.

13. The apparatus according to claim 1, wherein the multi-coil position sensor comprises two or more non-concentric coils.

14. The apparatus according to claim 13, wherein the two or more non-concentric coils are arranged so as to be mutually orthogonal.

15. Apparatus for electrical mapping of a pulmonary vein of a heart, comprising:
(a) a catheter, which comprises:
   (i) a curved section comprising a first position sensor, capable of generating fewer than six dimensions of position and orientation information, and one or more electrodes, adapted to measure an electrical property of the pulmonary vein; and
   (ii) a base section having a distal end attached to a proximal end of the curved section, the base section comprising, within 3 mm of the distal end thereof, a second position sensor, capable of generating six dimensions of position and orientation information; and
(b) a processor for determining fewer than six dimensions of position and orientation information of the first position sensor and six dimensions of position and orientation information of the second position sensor and combining the electrical property of the pulmonary vein for determining electrical abnormalities in the pulmonary vein for selecting target tissue to ablate in the pulmonary vein.

16. The apparatus according to claim 15, wherein the second position sensor is positioned within 1 mm of the distal end of the base section.

17. The apparatus according to claim 15, wherein the curved section comprises a material that is flexible, and maintains a substantially fixed length of the curved section.

18. The apparatus according to claim 15, wherein the curved section has an elasticity that is generally constant over at least a quarter of the curved section.

19. The apparatus according to claim 15, wherein the catheter comprises one or more ablation elements.

20. The apparatus according to claim 15, wherein at least one of the electrodes is adapted to perform ablation.

21. The apparatus according to claim 15, wherein the first position sensor is capable of generating exactly five dimensions of position and orientation information.

22. The apparatus according to claim 15, wherein the first position sensor is positioned in a vicinity of a distal end of the curved section.

23. The apparatus according to claim 15, wherein the curved section comprises a third position sensor in a vicinity of a center thereof, capable of generating fewer than six dimensions of position and orientation information.

24. The apparatus according to claim 15, wherein the curved section is shaped to generally conform to a shape of an interior surface of the pulmonary vein.

25. The apparatus according to claim 15, wherein the processor, generates an electrophysiological map of the pulmonary vein responsive to respective position signals generated by the first and second position sensors, and responsive to the electrical property.

26. Apparatus for electrical mapping of a pulmonary vein of a heart, comprising:
(a) a catheter, which comprises:
   (i) a curved section comprising a first position sensor in a vicinity of the distal end, capable of generating fewer than six dimensions of position and orientation information, and one or more electrodes, adapted to measure an electrical property of the pulmonary vein;
   (ii) a base section having a distal end attached to a proximal end of the curved section, the base section comprising, within 3 mm of the distal end thereof, a second position sensor, capable of generating six dimensions of position and orientation information; and
(b) a processor, for determining fewer than six dimensions of position and orientation information of the first position sensor and six dimensions of position and orientation information of the second position sensor and combining the electrical property of the pulmonary vein for determining electrical abnormalities in the pulmonary vein for selecting target tissue to ablate in the pulmonary vein and generating an electrophysiological map of the pulmonary vein responsive to respective position signals generated by the first and second position sensors, and responsive to the electrical property.

27. The apparatus according to claim 26, wherein the processor is adapted to calculate respective six-dimensional position and orientation coordinates of the one or more electrodes, responsive to the respective position signals.

28. Apparatus for electrical mapping of a chamber of a body of a subject, comprising:
(a) a catheter, which comprises:
   (i) a curved section comprising a first position sensor, capable of generating fewer than six dimensions of position and orientation information, and one or more electrodes, adapted to measure an electrical property of the chamber; and (ii) a base section having a distal end attached to a proximal end of the curved section, the base section comprising, within 3 mm of the distal end thereof, a second position sensor, capable of generating six dimensions of position and orientation information; and (b) a processor for determining fewer than six dimensions of position and orientation information of the first position sensor and six dimensions of position and orientation information of the second position sensor and combining the electrical property of the chamber for determining electrical abnormalities in the chamber for selecting target tissue to ablate in the chamber.

29. The apparatus according to claim 28, wherein the first position sensor is positioned in a vicinity of a distal end of the curved section.

30. The apparatus according to claim 28, wherein the curved section comprises a third position sensor in a vicinity of a center thereof, capable of generating fewer than six dimensions of position and orientation information.

31. A method for electrical mapping of a pulmonary vein of a heart, comprising:
introducing into the heart a catheter having a curved section and a base section, the base section having a distal end attached to a proximal end of the curved section;
generating, at a location on the curved section, a first position signal having fewer than six dimensions of position and orientation information, and, at a vicinity of the distal end of the base section, a second position signal having six dimensions of position and orientation information;
measuring, at one or more locations on the curved section, an electrical property of the pulmonary vein;
determining fewer than six dimensions of position and orientation information of the first position signal and six dimensions of position and orientation information of the second position signal and combining with the electrical property of the pulmonary vein;
determining electrical abnormalities in the pulmonary vein; and
selecting target tissue to ablate in the pulmonary vein.

32. The method according to claim 31, wherein generating the first position signal comprises generating the first position signal having exactly five dimensions of position and orientation information.

33. The method according to claim 31, wherein generating the first position signal comprises generating the first position signal at a vicinity of a distal end of the curved section.

34. The method according to claim 31, comprising generating, at a vicinity of a center of the curved section, a third position signal having fewer than six dimensions of position and orientation information.

35. The method according to claim 31, comprising calculating respective six-dimensional position and orientation coordinates of the one or more locations on the curved section at which the electrical property is measured, responsive to the first and second position signals.

36. The method according to claim 31, comprising generating an electrophysiological map of the pulmonary vein responsive to the first position signal, the second position signal, and the electrical property.

37. The method according to claim 31, wherein generating the second position signal comprises generating the second position signal at a location within 3 mm of the distal end of the base section.

38. The method according to claim 37, wherein generating the second position signal comprises generating the second position signal at a location within 1 mm of the distal end of the base section.

39. The method according to claim 31, comprising ablating tissue of the pulmonary vein responsive to the first position signal, the second position signal, and the electrical property.

40. The method according to claim 39, wherein ablating the tissue comprises determining a location of an electrical abnormality in the tissue responsive to the first position signal, the second position signal, and the electrical property, and ablating the tissue substantially at the location.

41. The method according to claim 31, wherein introducing the catheter into the heart comprises positioning the curved section within the pulmonary vein.

42. The method according to claim 41, wherein positioning the curved section within the pulmonary vein comprises positioning the base section within a left atrium of the heart.

43. The method according to claim 41, wherein positioning the curved section within the pulmonary vein comprises generally maintaining a point of attachment of the curved and base sections in a vicinity of an ostium of the pulmonary vein while mapping the pulmonary vein.

44. A method for electrical mapping of a chamber of a body of a subject, comprising:
introducing into the chamber a catheter having a curved section and a base section, the base section having a distal end attached to a proximal end of the curved section;
generating, at a location on the curved section, a first position signal having fewer than six dimensions of position and orientation information, and, at a vicinity of the distal end of the base section, a second position signal having six dimensions of position and orientation information;
measuring, at one or more locations on the curved section, an electrical property of the chamber;
determining fewer than six dimensions of position and orientation information of the first position signal and six dimensions of position and orientation information of the second position signal and combining with the electrical property of the chamber;
determining electrical abnormalities in the chamber; and
selecting target tissue to ablate in the chamber.

45. The method according to claim 44, wherein generating the first position signal comprises generating the first position signal at a vicinity of a distal end of the curved section.

46. The method according to claim 44, comprising generating, at a vicinity of a center of the curved section, a third position signal having fewer than six dimensions of position and orientation information.

* * * * *